(12) United States Patent
Case et al.

(10) Patent No.: US 10,286,148 B2
(45) Date of Patent: May 14, 2019

(54) USING PHYSIOLOGICAL DATA IN A MEDICAL DEVICE

(71) Applicant: Fenwal, Inc., Lake Zurich, IL (US)

(72) Inventors: Brian C. Case, Lake Villa, IL (US); Jonathan Prendergast, Palentine, IL (US); Joseph M. Foster, Buffalo Grove, IL (US); Witold Moskal, Park Ridge, IL (US)

(73) Assignee: FENWAL, INC., Lake Zurich, IL (US)

( * ) Notice: Subject to any disclaimer, the term of this patent is extended or adjusted under 35 U.S.C. 154(b) by 442 days.

(21) Appl. No.: 13/743,922

(22) Filed: Jan. 17, 2013

(65) Prior Publication Data

US 2013/0190674 A1 Jul. 25, 2013

Related U.S. Application Data

(60) Provisional application No. 61/589,755, filed on Jan. 23, 2012, provisional application No. 61/637,694, filed on Apr. 24, 2012.

(51) Int. Cl.
*G06Q 50/00* (2012.01)
*A61M 5/172* (2006.01)
(Continued)

(52) U.S. Cl.
CPC ............ *A61M 5/1723* (2013.01); *A61M 1/30* (2013.01); *G06F 19/3418* (2013.01); *G06F 19/3481* (2013.01)

(58) Field of Classification Search
CPC ........ G06Q 50/22; G06Q 50/24; G06Q 40/08; G06Q 10/10; G06F 19/322; G06F 17/30; G06F 19/30; G06F 19/32; G06F 19/321; G06F 19/324; G06F 19/325; G06F 19/326; G06F 19/328; G06F 19/3418; G06F 19/3456; G06F 19/34; G06F 19/3462;
(Continued)

(56) References Cited

U.S. PATENT DOCUMENTS 6,135,949 A * 10/2000 Russo .................. A61M 5/172
600/300
6,254,784 B1 7/2001 Nayak et al.
(Continued)

FOREIGN PATENT DOCUMENTS

WO WO-02/088930 11/2002

OTHER PUBLICATIONS

European Search Report for EP13152417 dated Apr. 20, 2016. 12 pages.
(Continued)

*Primary Examiner* — Tran N Nguyen
(74) *Attorney, Agent, or Firm* — Foley & Lardner LLP

(57) ABSTRACT

Systems and methods for using physiological data in a medical device are disclosed. The physiological data may be measured by a vital sign reader and received by a processing circuit associated with the medical device. The processing circuit may automatically adjust the operation of the medical device during a medical procedure based on the physiological data. In some implementations, the processing circuit may mirror a memory partition to a redundant storage device, allowing for uninterrupted execution of the medical procedure in the event of a memory failure condition.

13 Claims, 10 Drawing Sheets

(51) Int. Cl.
*A61M 1/30* (2006.01)
*G06F 19/00* (2018.01)
*G06Q 10/00* (2012.01)

(58) Field of Classification Search
CPC ............ G06F 19/3468; G06F 19/3475; G06F 19/3481; G06F 19/36; A61N 1/08; G16H 10/00; G16H 10/20; G16H 10/40; G16H 10/60; G16H 10/65; G16H 15/00; G16H 20/00; G16H 20/10; G16H 20/13; G16H 20/17; G16H 20/30; G16H 20/40; G16H 20/60; G16H 20/70; G16H 20/90; G16H 30/00; G16H 30/20; G16H 30/40; G16H 40/00; G16H 40/20; G16H 40/40; G16H 40/60; G16H 40/63; G16H 40/67; G16H 50/00; G16H 50/20; G16H 50/30; G16H 50/50; G16H 50/70; G16H 50/80; G16H 70/00; G16H 70/20; G16H 70/40; G16H 70/60; G16H 80/00

See application file for complete search history.

(56) References Cited

U.S. PATENT DOCUMENTS

| | | | |
|---|---|---|---|
| 6,551,266 B1* | 4/2003 | Davis, Jr. | 604/6.09 |
| 6,796,956 B2* | 9/2004 | Hartlaub | A61M 5/14276 604/65 |
| 8,255,238 B2 | 8/2012 | Powell et al. | |
| 2007/0175827 A1 | 8/2007 | Wariar | |
| 2009/0069785 A1* | 3/2009 | Miller | A61M 5/14244 604/500 |
| 2010/0049542 A1 | 2/2010 | Benjamin et al. | |
| 2011/0257798 A1* | 10/2011 | Ali et al. | 700/282 |

OTHER PUBLICATIONS

"Lock (computer science)," Wikipedia, Jan. 17, 2012 (XP055370138).
European Office Action, EP App. No. 13152417.5, Fenwal, Inc., 9 pages (dated May 16, 2017).

* cited by examiner

USING PHYSIOLOGICAL DATA IN A MEDICAL DEVICE

CONTINUITY DATA

The present application claims priority to U.S. Provisional Patent Application No. 61/589,755 entitled "USING PHYSIOLOGICAL DATA IN A MEDICAL DEVICE" filed Jan. 23, 2012, the entirety of which is hereby incorporated by reference. The present application also claims priority to U.S. Provisional Patent Application No. 61/637,694 entitled "MEMORY MANAGEMENT IN A MEDICAL DEVICE" filed Apr. 24, 2012, the entirety of which is hereby incorporated by reference.

BACKGROUND

The present disclosure relates generally to the field of medical devices. More specifically, the disclosure relates to using physiological data in a medical device from one or more measurement devices.

In some medical settings, a patient's vital signs and/or other physiological measurements may be measured by any number of disparate measurement readers. For example, a patient's blood pressure may be measured by a sphygmomanometer, the patient's pulse rate measured by a heart rate monitor, and the patient's body temperature measured by a thermometer. In some cases, a medical professional may operate the measurement readers to monitor the user's overall progress during a medical procedure. For example, a nurse may periodically check the patient's vital signs while the patient undergoes the procedure.

SUMMARY

One implementation relates to a method for using physiological data in a medical device. The method includes generating, by a processing circuit, a start procedure command configured to cause the medical device to begin a medical procedure on a subject. The method also includes receiving, at the processing circuit, physiological data from a measurement device, the physiological data being indicative of a physiological condition of the subject during the medical procedure. The method further includes analyzing, by the processing circuit, the physiological data. The method yet further includes generating, by the processing circuit, a control command for the medical device based in part on the analyzed physiological data.

Another implementation relates to a system for using physiological data in a medical device. The system includes a processing circuit operable to generate a start procedure command configured to cause the medical device to begin a medical procedure on a subject. The processing circuit is also operable to receive physiological data from a measurement device, the physiological data being indicative of a physiological condition of the subject during the medical procedure. The processing circuit is further operable to analyze the physiological data. The processing circuit is yet further configured to generate a control command for the medical device based in part on the analyzed physiological data.

A further implementation relates to an apheresis machine. The apheresis machine includes a separation component configured to separate blood into blood components and a processing circuit configured to control the separation component. The processing circuit is also configured to generate a start procedure command configured to cause the separation component to begin separating blood from a subject into blood components. The processing circuit is further configured to receive physiological data from a measurement device, the physiological data being indicative of a physiological condition of the subject during the apheresis procedure. The processing circuit is additionally configured to analyze the physiological data. The processing circuit is yet further configured to generate a control command for the apheresis machine based in part on the analyzed physiological data.

BRIEF DESCRIPTION OF THE DRAWINGS

Features, aspects, and advantages of the present invention will become apparent from the following description, appended claims, and the accompanying exemplary implementations shown in the drawings, which are briefly described below.

DETAILED DESCRIPTION

Figure 1:
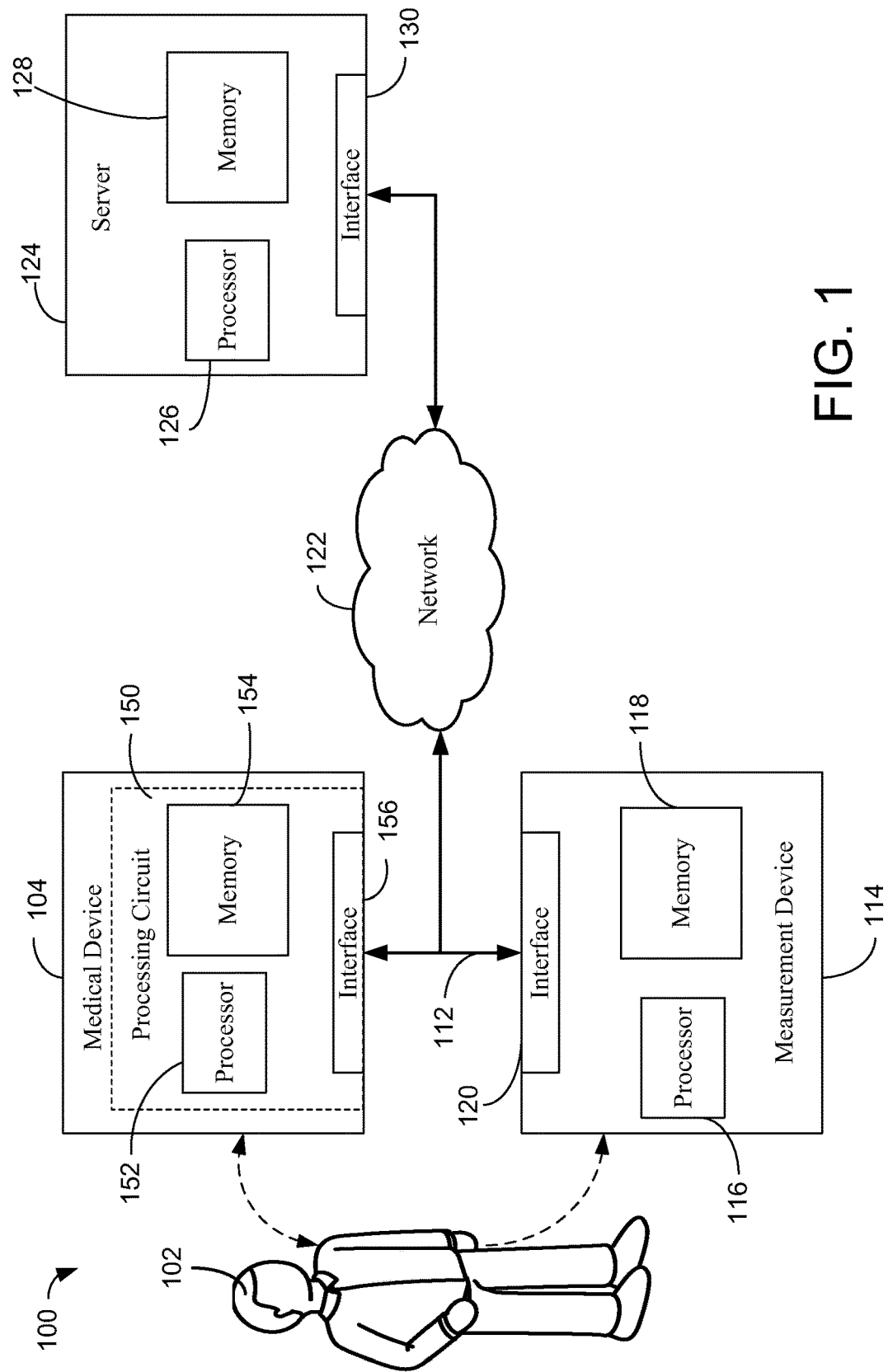
FIG. 1 is a block diagram of a computing system, in accordance with an exemplary implementation.

It is to be understood that the following detailed description is exemplary and explanatory only, and is not restrictive of the invention as claimed.

According to various aspects of the present disclosure, physiological data may be integrated into a medical device used to perform a medical procedure on a patient. In some implementations, the integrated physiological data may be used by the medical device to create an electronic record of the medical procedure. For example, the physiological data and performance characteristics of the medical device may be time stamped during the procedure to record how the patient reacted to different operational states of the medical device. In some cases, the electronic records may be sent to a central server for further data storage and processing. In further implementations, the integrated physiological data may be used by the medical device to generate alerts. For example, an alert may be generated if the patient's blood pressure drops below an acceptable threshold during the medical procedure. In further implementations, the medical device may be configured to automatically adjust one or more of its operating parameters based in part on the physiological data.

In one implementation, the medical device may be a blood apheresis machine. Example blood apheresis machines include the ALYX™ System, the AMICUS™ Separator, and the AUTOPHERESIS-C™ System, all available from Fenwal, Inc., at 3 Corporate Drive, Lake Zurich, Ill. 60047, as well as other apheresis machines. In general, blood apheresis machines operate to separate blood components from a blood donor or a patient undergoing therapy. For example, blood may be separated into plasma, red blood cells, white blood cells, or platelets. Blood components may be extracted by an apheresis machine by first drawing blood from a patient or donor, separating the components using a separation technique (e.g., centrifugation, membrane filtration, or the like), and then returning uncollected blood components to the blood stream of the donor or patient. For donation procedures, the collected blood components may be used as part of the therapy of other patients. For example, separated red blood cells may be transfused to a patient having sickle cell anemia. In such a case, transfusing whole blood may have detrimental health effects on the anemic patient. Similarly, an apheresis machine may be used to treat certain blood-related disorders. For example, autoantibodies may be removed from a patient suffering from an autoimmune disorder using an apheresis machine that removes plasma from the patient's blood.

An apheresis machine may perform any number of operations to facilitate an apheresis procedure. For example, an apheresis machine may regulate the flow rate of blood entering and/or leaving a patient or donor, regulate the dosage of a medicament administered to the subject, provide a bolus of saline to the subject, change a citrate infusion rate, or perform other operations. During an apheresis procedure, saline may be used in some cases to replace fluid volume lost as a result of separating out blood components from the donor or patient. The apheresis machine may also administer an anticoagulant, such as anticoagulant sodium citrate (ASC), anticoagulant citrate dextrose (ACD), or a similar anticoagulant. The administration of an anticoagulant is required to prevent the formation of blood clots within the disposable flow paths during the apheresis procedure.

The various operations of an apheresis machine may affect a patient's vital signs and/or other physiological conditions. For example, administration of a citrate-based anticoagulant by an apheresis machine may affect a patient or donor's blood pressure and/or pulse rate. Typically, different patients or donors have differing tolerances for citrate-based anticoagulants. In many cases, a person's tolerance for a citrate-based anticoagulant may be estimated as a function of the person's body weight. However, a donor or patient's vital signs is monitored during an apheresis procedure so that the person does not have an adverse reaction. For example, an adverse reaction to a citrate-based anticoagulant may result in an increased pulse rate and/or a decreased blood pressure.

In other examples, lower weight people tend to be more susceptible to an adverse reaction from the volume of blood removed during an apheresis procedure. In such a case, the person may exhibit a drop in blood pressure or may even faint during the procedure. A patient may also exhibit an abnormal pulse rate or blood pressure if the flow rate through the apheresis machine is too high or low.

In a traditional apheresis procedure, a health care professional may periodically monitor a subject's vital signs and/or other physiological conditions to ensure that the subject is not having an adverse reaction. In some cases, the health care professional may record the subject's vital signs and enter them into a computer system and/or retain hard-copies for record keeping purposes. Similarly, if the healthcare professional believes the subject is having an adverse reaction during the procedure, they may adjust the operation of the apheresis machine accordingly. For example, a health-care provider may lower the dosage of citrate-based anticoagulant and/or administer a bolus of saline to a subject having an adverse reaction to the anticoagulant. However, such actions are dependent on the health care professional, leading to the possibility of human error.

According to various implementations, data used in a medical device, such as an apheresis machine, may also be stored in segregated memory locations. In some implementations, different read/write permissions may be applied to the memory locations based on the operational state of the medical device. For example, a first memory location may store a routine that causes the device to perform a medical procedure and a second memory location may store operational data regarding the operation of the medical device. During execution of the routine, the first memory location may be allowed to write data to the second memory location. For example, the routine may be able to transfer data regarding the medical procedure to the second memory location. However, the second memory location may be prevented from writing data to the first memory location during performance of the medical procedure. Thus, the first memory location may be protected from potential sources of failure during the medical procedure. Once the routine stops executing and the medical procedure concludes, the second memory location may be able to write data to the first memory location. For example, an update for the routine stored at the second memory location may be installed to the first memory location, if the device is not being used to perform a medical procedure.

Any data that is not critical to the execution of a routine that performs a medical procedure may be stored in a separate memory location from the routine. In some implementations, the non-critical data may include operational data for the medical device. Operational data may include, but is not limited to, diagnostic data, debugging data, log data indicative of activities conducted during the apheresis procedure, and other such data. Other example forms of data that may not be critical to the performance of a medical procedure include communication routines (e.g., to receive and/or transfer data from the medical device to another electronic device), update routines (e.g., to update a routine that performs a medical procedure, to update a communication routine, etc.), and physiological measurements taken from a living subject.

Memory locations in a medical device may also be mirrored or synchronized, to provide redundant data storage. For example, a routine that causes the device to perform a medical procedure may be stored in redundant memory locations (e.g., the contents of a first memory location may be mirrored to one or more other memory locations). In some cases, the redundant memory locations may be stored on separate memory devices (e.g., data storage devices that are physically separated). For example, copies of a routine may be mirrored across two or more different hard disks. If a disk failure occurs, the routine may continue to execute by running from the mirrored hard disk.

Referring now to FIG. 1, an exemplary computer system 100 is shown. Computer system 100 may be used in a medical setting to perform a medical procedure involving subject 102. System 100 includes a medical device 104 configured to perform the medical procedure and one or more physiological measurement devices, such as measurement device 114, configured to monitor the vital signs and/or other physiological conditions of subject 102 during the procedure. In some implementations, measurement device 114 and/or medical device 104 may communicate via network 122 with a server 124 before, during, and/or after the medical procedure is performed. For example, medical device 104 may transmit data via network 122 regarding the performance of the procedure to server 124 (e.g., the subject's physical state, the operational states of medical device 104, etc.). Similarly, server 124 may transmit data via network 122 to medical device 104, such as a routine to load or update existing software on medical device 104, subject data regarding subject 102 (e.g., the patient's medical history, chart information, etc.), and other operational data. Medical device 104 and measurement device 114 may be integrated within a single housing, or each disposed in its own separate housing. Device 104 and measurement device 114 may share a common power supply circuit located within a portable housing, and optionally other electronic components (e.g., memory, a processor, a circuit board, etc.). Device 104 and measurement device 114 may be portions of a single piece of medical equipment.

Medical device 104 may be any form of electronic device configured to perform a medical procedure on subject 102. In non-limiting examples, medical device 104 may be a device that administers a medicament to subject 102, extracts fluid or tissue from subject 102, implants an object into subject 102, or captures a medical image of subject 102. For example, medical device 104 may be a dialysis machine (e.g., a hemodialysis machine, a hemofiltration machine, etc,), an infusion pump, or a drug delivery system, in some implementations. In various implementations, medical device 104 may be an apheresis machine configured to draw blood from subject 102 (i.e., subject 102 is a donor or receiver of blood components). In some implementations, medical device 104 may use measurements taken from subject 102 to control the medical procedure. The measurements may be taken directly by medical device 104 or may be received by medical device 104 via data link 112 from measurement device 114. For example, medical device 104 may use the body temperature, pulse rate, blood pressure, respiratory rate, blood glucose level, pupil dilation, pulse oximetry information, ECG information, or other physical characteristic of subject 102 during the medical procedure.

Measurement device 114 may be any form of electronic device configured to measure one or more vital signs and/or other physiological conditions of subject 102. A measured vital sign may be any physiological characteristic of subject 102 indicative of the physical condition of subject 102. For example, measurement device 114 may measure the body temperature, pulse rate, blood pressure, respiratory rate, blood glucose level, pupil dilation, pulse oximetry information, ECG information, or other physical characteristic of subject 102. In some implementations, measurement device 114 may measure multiple physiological characteristics of subject 102. For example, measurement device 114 may measure both the blood pressure and pulse rate of subject 102. In another example, measurement device 114 may include a blood pressure cuff to be disposed around subject 102's arm and inflated with air as part of a blood pressure measurement of subject 102.

Medical device 104 may include a processor 152, a memory 154, and an interface 156, i.e., a processing circuit 150. Processor 152 may include one or more microprocessors, application-specific integrated circuits (ASICs), field programmable gate arrays (FPGAs), other forms of processing components, or a combination thereof. Memory 154 may include any form of electronic, optical, magnetic, or other form of data storage configured to provide processor 152 with program instructions. Memory 154 may further include a floppy disk, CD-ROM, DVD, magnetic disk, memory chip, ROM, RAM, EEPROM, EPROM, flash memory, optical media, other forms of non-transitory media, or any other suitable memory from which processor 152 can read instructions. When executed by processor 152, the instructions cause medical device 104 to perform some or all of the functions described herein. In various implementations, data stored in memory 154 may be segregated across different memory locations (e.g., in different memory storage devices, in different partitions of the same storage device, etc.). Data in memory 154 may also be stored redundantly, in some implementations. For example, data may be mirrored in memory 154 to a plurality of memory storage devices, allowing for continuous operation of medical device 104, if one of the storage devices experiences a failure.

Medical device 104 may include interface 156 configured to receive and/or transmit data to other electronic devices. For example, medical device 104 may utilize interface 156 to provide a data link 112 between medical device 104 and measurement device 114. Interface 156 may provide a hardwired connection, wireless connection, or a combination thereof between medical device 104 and other electronic devices. In some implementations, data link 112 may be a wireless connection between interface 156 of medical device 104 and an interface 120 of measurement device 114 (e.g., interface 156 communicates with measurement device 114 via a WiFi, cellular, near-field, radio, Bluetooth, optical, or other form of wireless connection). In other implementations, data link 112 may be a hardwired connection between interface 156 of medical device 104 and interface 120 of measurement device 114. For example, data link 112 may be provided via one or more cables (e.g., a CAT5 cable, coaxial cable, USB cable, or similar hardwired connection). Data link 112 may be bidirectional or unidirectional, according to various implementations. For example, measurement device 114 may transmit physiological data to medical device 104 in response to receiving a request for data from medical device 104 or unprompted, according to various implementations.

Similar to medical device 104, measurement device 114 may also include a processor 116 and a memory 118, i.e., a processing circuit. Memory 118 may store instructions that, when executed by processor 116, cause processor 116 to execute some or all of the operations described herein. Measurement device 114 may monitor subject 102 continuously or periodically, according to various implementations. In response to receiving a measurement, measurement device 114 may provide physiological data to medical device 104 via interface 120. For example, measurement device 114 may measure the pulse rate of subject 102 and provide it to medical device 104 via data link 112.

In some implementations, medical device 104 may be configured to utilize physiological data received from measurement device 114 to alert a healthcare professional and/or adjust its operation. For example, medical device 104 may generate an audible sound, to alert a healthcare professional to attend subject 102. In another example, medical device 104 may adjust its control over the medical procedure based in part on the physiological data. For example, if medical device 104 is an apheresis machine, medical device 104 may adjust a citrate infusion rate to subject 102 provided by an infusion pump and/or provide a bolus of saline to subject 102, based on a determination that the blood pressure of subject 102 has dropped below a threshold value. In this way, subject 102, measurement device 114, and medical device 104 may form a feedback control loop during the medical procedure.

Physiological data generated by measurement device 114 may be used for record keeping purposes, according to various implementations. For example, measurement device 114 may associate a timestamp with measurements taken from subject 102. Similarly, medical device 104 may associate a timestamp with physiological data received from measurement device 114. In some implementations, server 124 may receive the physiological data from measurement device 114 and/or from medical device 104 and store an electronic record of the reaction of subject 102 to the medical procedure. In some implementations, server 124 may also receive operational data from medical device 104 via network 122. Operational data may include any data indicative of the operational state of medical device 104 during the medical procedure. For example, the operational data may include, but is not limited to, a fluid flow rate, a citrate infusion rate, a dosage of substance administered to subject 102 (e.g., a dosage of medicament, saline, blood, blood component, anticoagulant, or other fluid). In some implementations, the operational data may be time stamped, allowing a record of the operation of medical device 104 to be generated. Medical device 104 may be configured to time stamp the operational data at periodic or intermittent intervals, e.g., at least every 10 minutes, at least every 15 minutes, etc.

Server 124 may be any form of computing device or set of computing devices configured to store and communicate electronic data. For example, server 124 may be a personal computer, a mainframe, a cloud-computing environment, or a data center. In some implementations, server 124 may be a portable electronic device, such as a smartphone, a personal data assistant, a tablet computer, a laptop computer, or the like. Server 124 may include a processing circuit that includes a processor 126 and a memory 128 that stores instructions for processor 126. Server 124 may also include interface 130 configured to communicate with network 122 via a wireless or hardwired connection, according to various implementations.

Network 122 may be any form of computer network that relays information between medical device 104, server 124, and/or measurement device 114. For example, network 122 may include the Internet and/or other types of data networks, such as a local area network (LAN), a wide area network (WAN), a cellular network, satellite network, or other types of data networks. Network 122 may also include any number of intermediary computing devices (e.g., computer, servers, routers, network switches, etc.) that are configured to receive and/or transmit data within network 122.

Server 124 may receive and store physiological data generated by measurement device 114 and/or operational data generated by medical device 104 in memory 128, in some implementations. In further implementations, memory 128 may store information about subject 102 and provide subject data to medical device 104. For example, subject data may include demographics information about subject 102 (e.g., height, weight, gender, etc.), medical information about subject 102 (e.g., allergies, symptoms, diseases, medical conditions, etc.), or other information that may be provided to other electronic devices by server 124. In some implementations, medical device 104 may adjust its operation based in part on subject data received from server 124. Server 124 may also provide installation data to medical device 104 via network 122 (e.g., to install, update, and/or remove software loaded in memory 154 of medical device 104). Server 124 may be configured to communicate with medical device 104 via any number of different networking protocols. For example, server 124 may communicate with medical device 104 via an HTTP connection, FTP connection, SSH connection, a telnet connection, combinations thereof, or other similar networking protocols. In some implementations, server 124 may relay data between medical device 104 and another electronic device. For example, server 124 may be a device that communicates with medical device 104 within the same medical facility and relays information between medical device 104 and a server of the manufacturer of medical device 104 via the Internet.

Figure 2:
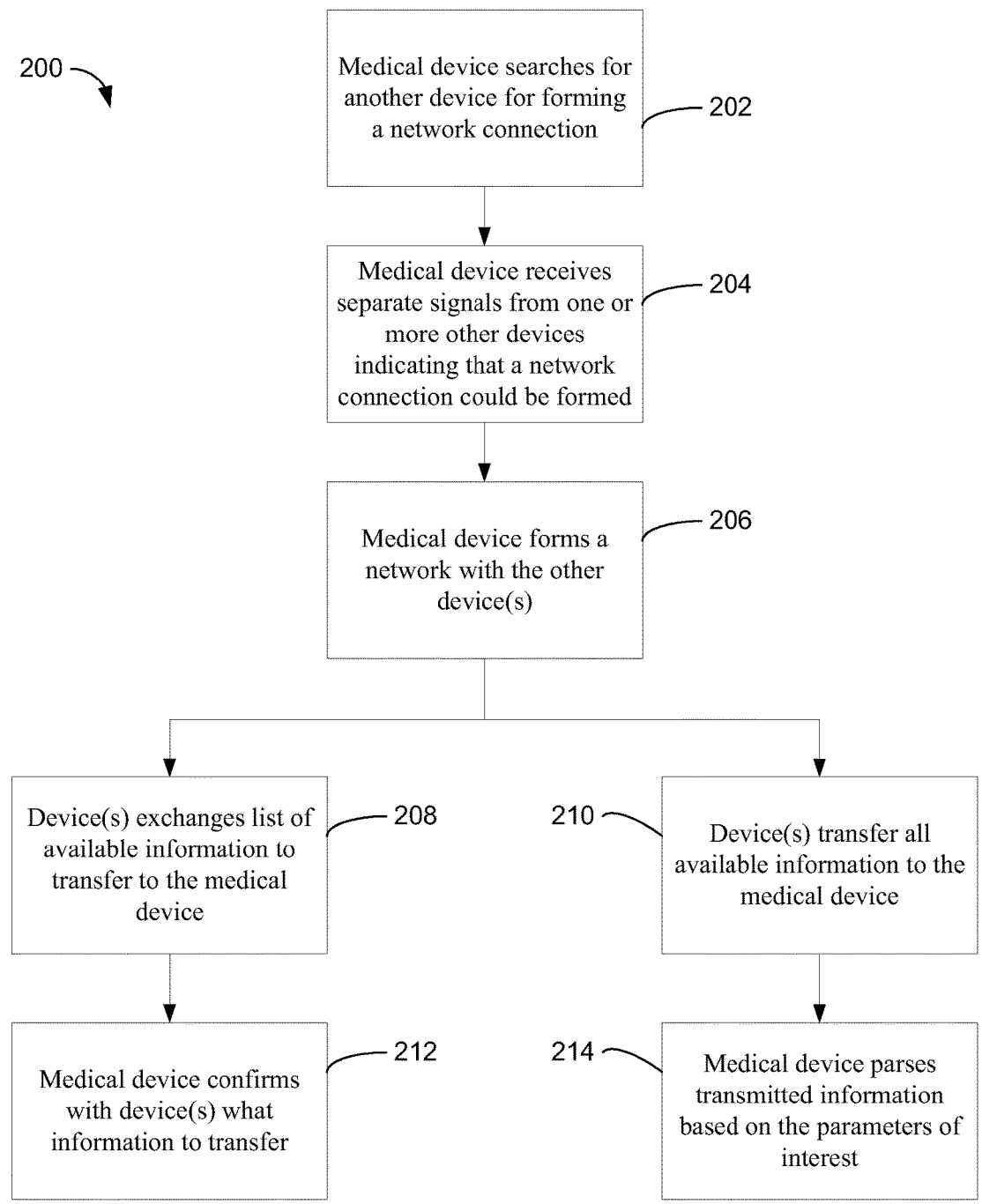
FIG. 2 is a process for interfacing a medical device with one or more measurement devices, in accordance with an exemplary implementation.

Referring now to FIG. 2, a process 200 for interfacing a medical device with one or more measurement devices is shown, according to various implementations. Process 200 may be utilized, for example, to interface medical device 104 of FIG. 1 with measurement device 114, in one implementation. While process 200 is shown with reference to a medical device initiating a data connection with another device (e.g., a vital sign reader or other physiological measurement device), the other device may initiate the connection, in other implementations.

Process 200 may include a medical device searching for another device for forming a network connection (block 202). For example, the medical device may search for an eligible vital sign reader with which to interface. In some implementations, the medical device may search for another device by broadcasting a wireless signal. In one example, an apheresis machine may broadcast a signal indicating that it is ready to form a connection with an electronic sphygmomanometer. In other implementations, the medical device may send a query or other status message to the other device via a hardwired connection. For example, a medical professional may connect a medical device to a vital sign reader via a USB cable. The medical device may then send a message to the measurement device to determine if the reader is ready to establish a data link.

In some implementations, a security mechanism may control which devices are able to establish a data link. For example, an identifier of a vital sign reader or other measurement device may be registered with a medical device, or vice-versa, to determine eligibility to establish a data link. In some implementations, the identifier may be associated with a password. For example, the medical device may be utilized to send an identifier and password to a vital sign reader, to establish a data link between the devices.

Process 200 may include the medical device receiving an indication from one or more devices that a connection can be formed (block 204). A device may not be eligible to establish a connection with a medical device for any number of different reasons. For example, a vital sign reader may be ineligible to interface with a medical device because the reader is turned off, is running a diagnostic routine, is in an error state, is not registered with the medical device, or the medical device provides the wrong credentials to the reader. If the device is active, ready to establish a connection, and/or the medical device provides proper credentials, the device may return an indication that the data link may be formed.

Process 200 may include forming a network between the medical device and the one or more other devices (block 206). In some implementations, the network connection between the medical device and another device may be a direct connection. In other words, the data connection between the medical device and the other device may not go through any intermediary devices. In other implementations, the data connection may pass through one or more intermediary devices (e.g., computers, routers, switches, etc.) between the medical device and the device to which it is connecting. For example, a medical device may interface with a vital sign reader via a WiFi LAN of a medical clinic.

Process 200 may include the one or more devices providing a list of available information to the medical device (block 208). The list may include some or all of the different types of data values available from the other device and/or other parameters to control the delivery of data to the medical device. For example, the other device may measure a subject's blood pressure and pulse rate. In some cases, the list may include parameters that may be used by the medical device to control how often data values are to be provided to the medical device, the units of measure for the data values (e.g., Celsius vs. Fahrenheit, etc.), how often the other device is to measure a subject's vital signs or other physiological readings, or any other type of parameter. In some implementations, the list may be provided in response to a data link being established between the medical device and the other device. In other implementations, the list may be provided to the medical device in response to the medical device providing a request for available data to the other device.

Process 200 may include the medical device providing an indication of what information is to be transferred from the other device to the medical device (block 212). For example, the medical device may provide an indication to the other device that the subject's blood pressure is to be sent, but not the subject's pulse rate. In another example, the indication may specify that blood pressure readings are to be sent every thirty seconds to the medical device.

Alternatively, or in addition to block 208, 212, process 200 may include the other device transferring all available data to the medical device (block 210). For example, a thermometer device may provide body temperature readings of a subject to the medical device, in lieu of allowing the medical device to select to receive temperature readings. In some implementations, the transfer of data may be automatic (i.e., without further user intervention), in response to a data connection being established. In other implementations, the other device may provide data to the medical device in response to receiving a request for the data. Whether the other device provides the data immediately or allows the medical device to select which data is provided may be controlled by a parameter, in some implementations. For example, a user of the medical device or other device may set a parameter to control how the two devices interface.

Process 200 may include the medical device parsing the transmitted data based on parameters of interest (block 214). In cases in which the other device provides all available data to the medical device, the data may include extraneous data that is not of use to the medical device. For example, the medical device may utilize blood pressure measurements, but not pulse rate measurements. If the other device provides both blood pressure measurements and pulse measurements to the medical device, the medical device may parse the received data to only utilize the received blood pressure measurements. In some implementations, the data of interest for a medical device may change over time (e.g., as a function of the current operating state of the medical device, based on a user-set parameter, etc.).

Figure 3:
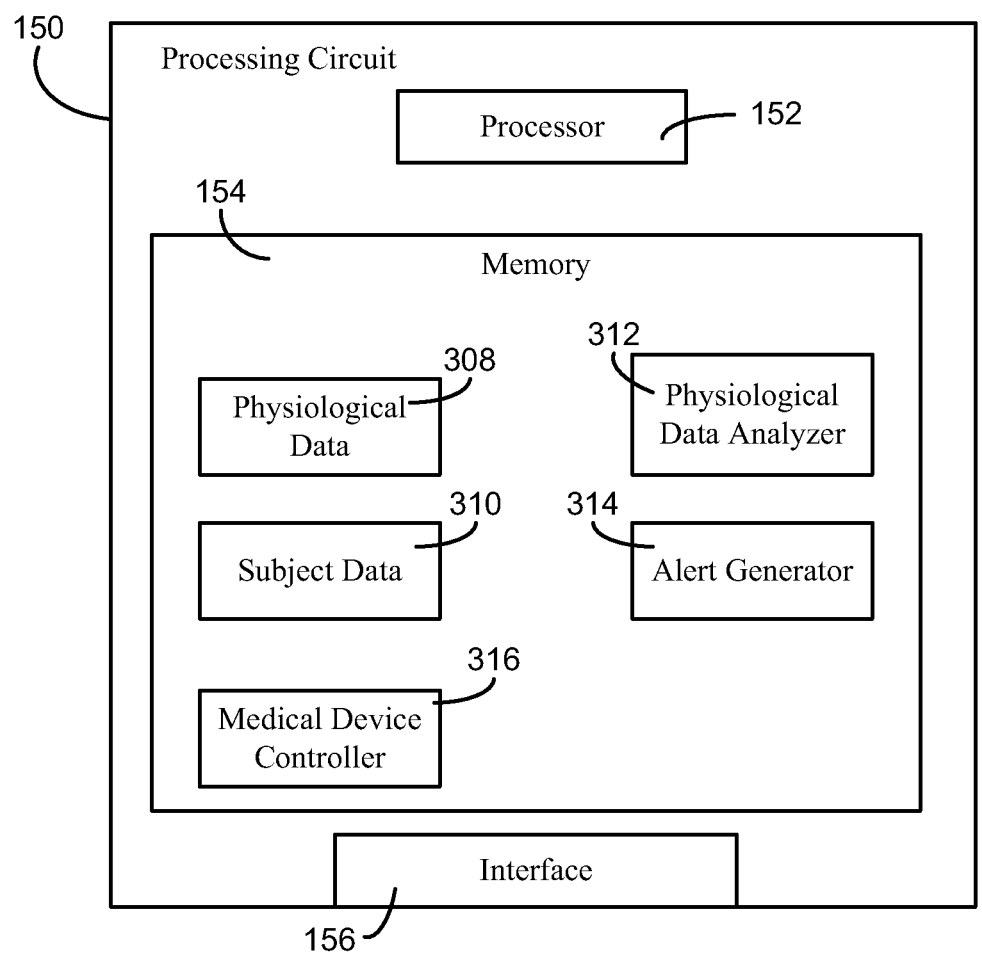
FIG. 3 is a block diagram of a processing circuit of a medical device, in accordance with another exemplary implementation.

Referring now to FIG. 3, a block diagram of a processing circuit 150 is shown, according to various implementations. Processing circuit 150 may be within or a part of a medical device, such as medical device 104 shown in FIG. 1. In some implementations, processing circuit 150 may be part of a blood apheresis or other blood collection device. As shown, memory 154 is configured to store data or computer code relating to the activities described herein. For example, memory 154 is shown to include a physiological data analyzer 312, alert generator 314, and a medical device controller 316, which may be implemented using computer code (e.g., executable code, object code, source code, script code, machine code, etc.) configured for execution by processor 152. When executed by processor 152, processing circuit 150 is configured to complete the activities described herein.

Processing circuit 150 may include additional hardware circuitry for supporting the functions of processing circuit 150. For example, processing circuit 150 may include interface 156 for communicating with other electronic devices (e.g., a vital sign reader, a remote server, etc.). In another example, interface 156 may include circuitry to transmit and/or receive from a user interface device. In general, a user interface device refers to any form of electronic device configured to receive and/or provide sensory data to a user. Example user interfaces include electronic displays, speakers, keypads, touch screen displays, pointing devices, and the like. Interface 156 may provide a wireless connection, a hardwired connection, or both, according to various implementations. In some implementations, interface 156 may receive physiological data 308 from one or more vital sign readers or other physiological measurement devices and store the data in memory 154. In further implementations, interface 156 may receive subject data 310 from a user interface device and/or a remote server and store the data in memory 154. Similarly, interface 156 may be configured to provide data from processing circuit 150 to other devices. For example, interface 156 may provide alerts, control commands, and/or report data to other electronic devices or components.

Memory 154 is shown to include physiological data 308. Physiological data 308 may include, but is not limited to, measurements of a subject's body temperature, blood pressure, respiratory rate, pulse rate, or other physical characteristics of the subject. According to various implementations, physiological data 308 may be received by processing circuit 150 from one or more vital sign readers and/or other physiological measurement devices via interface 156. Physiological data 308 may include timestamp information, in some cases. For example, processing circuit 150 may correlate the current time and/or date with a vital sign measurement (e.g., processing circuit 150 may timestamp physiological data 308 when the data is received). In another example, the timestamp may be created by the measurement device that took the measurement (e.g., a vital sign reader time stamps the measurements).

In some implementations, memory 154 may include subject data 310. In general, subject data 310 may include demographics information, medical history, or other forms of information relating to the subject undergoing a medical procedure performed by the medical device of processing circuit 150. In one implementation, subject data 310 may be entered by the subject or a healthcare professional via a user interface device connected to processing circuit 150 via interface 156. In other implementations, subject data 310 may be received from a remote server. For example, subject data 310 may be received via interface 156 from a server of a blood center or other medical facility, a server that services multiple facilities, or a server of an insurance company.

Memory 154 may include physiological data analyzer 312. Physiological data analyzer 312 may be configured to determine whether the subject of the medical procedure is having an adverse reaction to the medical procedure. In some implementations, physiological data analyzer 312 may compare physiological data 308 to one or more threshold values, to determine whether the subject is having an adverse reaction. For example, physiological data analyzer 312 may determine that the subject's blood pressure has dropped below an acceptable level based on physiological data 308. In another example, physiological data analyzer 312 may determine that the subject's pulse rate is above an acceptable level. A physiological data value may have an upper threshold, lower threshold, or both. In some implementations, physiological data analyzer 312 may determine whether a vital sign or other physiological data value in physiological data 308 is within a certain range of values (e.g., physiological data analyzer 312 may use multiple upper or lower thresholds). In such a case, the various ranges may correspond to different corrective measures. For example, if the subject's blood pressure drops below a first lower threshold, the medical device may administer a bolus of saline and/or adjust a citrate infusion rate. If the subject's blood pressure drops below an even lower threshold, processing circuit 150 may issue an alert to a healthcare professional.

In some implementations, physiological data analyzer 312 may utilize subject data 310 to determine acceptable thresholds for physiological data 308. For example, the subject's age, weight, gender, and other characteristics may affect the physiological measurement thresholds used by physiological data analyzer 312. In further implementations, some or all of the thresholds used by physiological data analyzer 312 may be hardcoded in memory 154 or specified by a healthcare professional via a user interface device. For example, a nurse overseeing the medical procedure may specify that an alert should be issued if a patient's blood pressure drops below a certain threshold.

Memory 154 may include medical device controller 316. Medical device controller 316 is configured to generate control commands for the various components of the medical device of processing circuit 150. Medical device controller 316 may generate any number of control commands to initiate a procedure (e.g., a start procedure command), perform the procedure, adjust how the procedure is performed, or end the procedure, either at the end of the procedure or prematurely (e.g., a stop procedure command). In various examples, medical device controller 316 may generate a control command for a motor, pump, actuator, electrode, combinations thereof, or any other component of the medical device. In some implementations, medical device controller 316 may generate a command to adjust the flow of a fluid (e.g., blood, blood component, saline, medicament, anticoagulant, or other fluid) to or from the subject. For example, if the medical device is an apheresis machine, medical device controller 316 may generate a command to provide a bolus of saline to a subject undergoing an apheresis procedure.

In some implementations, medical device controller 316 may generate a control based in part on the analysis of physiological data 308 by physiological data analyzer 312. In other words, physiological data 308, physiological data analyzer 312, and medical device controller 316 may form a feedback control loop. For example, physiological data analyzer 312 may utilize a setpoint or range of setpoints for physiological data 308. In such a case, medical device controller 316 may issue a control command to reduce the difference between physiological data 308 and the setpoint or range of setpoints. In one example, medical device controller 316 may adjust the amount of anticoagulant provided to a subject and/or provide a bolus of saline to the subject, based on the subject's blood pressure or pulse rate. In a further example, medical device controller 316 may issue a control command that causes the apheresis machine to pause the procedure or abort the procedure entirely. In some implementations, medical device controller 316 may issue a control command that causes a replacement fluid to be switched (e.g., switching between albumin and fresh frozen plasma, etc.).

In some implementations, medical device controller 316 may generate operational data indicative of the operational state of the medical device. For example, medical device controller 316 may record data relating to actions performed by the medical device and/or control commands issued by medical device controller 316. In some cases, the operational data may be time stamped by medical device controller 316. For example, medical device controller 316 may record when a bolus of saline was provided to a subject. In this way, a record of the operation of the medical device may be created. Processing circuit 150 may provide the operational data and/or physiological data 308 to another electronic device, such as an electronic display or a networked server.

Memory 154 may include alert generator 314, in some implementations. Similar to medical device controller 316, alert generator 314 may generate an alert based in part on the analysis of physiological data 308 by physiological data analyzer 312. For example, alert generator 314 may generate an alert if the subject's blood pressure drops below a certain threshold. In various implementations, an alert may be generated by alert generator 314 in addition to, or in lieu of, medical device controller 316 adjusting an operation of the medical device.

In some cases, an alert generated by alert generator 314 may be provided to a user interface device via interface 156. For example, alert generator 314 may cause a sound to be produced by a speaker. In another example, alert generator 314 may cause indicia to be displayed on an electronic display. In further cases, an alert generated by alert generator 314 may be provided to a mobile device operated by a healthcare professional (e.g., as a text message, status alert, automated phone call, etc.). In this way, a healthcare professional may be alerted if the subject has an adverse reaction to the medical procedure.

Figure 4:
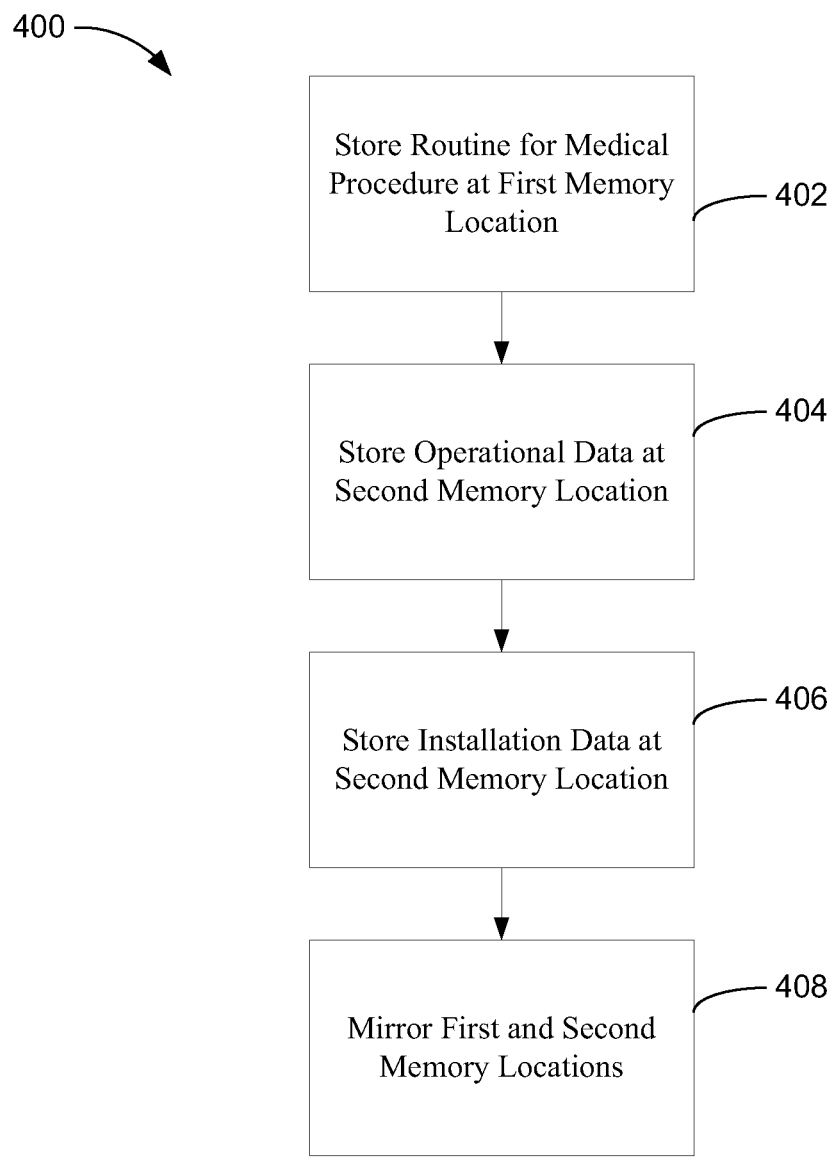
FIG. 4 is flow diagram of a process for managing memory storage in a medical device, according to an exemplary implementation.

Referring now to FIG. 4, a process 400 for managing memory storage in a medical device is shown, according to one implementation. Process 400 may be implemented by any medical device having a processor that executes instructions stored within a memory. For example, process 400 may be implemented by medical device 104 shown in FIG. 1. In some implementations, process 400 may be implemented by an apheresis machine configured to collect blood components from a donor. In general, process 400 allows for the redundant storage of data.

Process 400 may include storing a routine for a medical procedure at a first memory location (block 402). The routine, when executed by one or more processors, may cause a medical device to perform a medical procedure. For example, an apheresis machine may execute a stored donor procedure routine during collection of blood components from a donor. In some implementations, the first memory location may be an allocated partition of a memory storage device. For example, the first memory location may be a hard drive partition. In other implementations, the first memory location may itself be a memory storage device. For example, a separate hard drive may be used to store the routine for the medical procedure.

Various security settings may be used to restrict and/or prevent access to the first memory location. In some implementations, access to the first memory location may be prevented during execution of the medical procedure routine. In other words, only the medical procedure routine may change the data stored in the first memory location while the routine is executing (i.e., users and other applications may be prevented from changing the data in the first memory location). In some implementations, access to the first memory location may also be restricted based on an operational mode for the medical device. For example, software changes to the first memory location may be allowed if the medical device is in a service mode. In further implementations, security credentials may be required to access the first memory location. For example, a technician may be required to supply a password and/or utilize software from the device manufacturer to make changes to the first memory location.

Process 400 may include storing operational data at a second memory location (block 404). Similar to the first memory location, the second memory location may be a partition of a storage device or may itself be its own storage device. Operational data may include any data generated during operation of the medical device. For example, operational data may include data regarding physiological measurements taken from the subject of a medical procedure, log data, debugging data, event data, or any other data indicative of the operational condition of the medical device.

In some implementations, different security settings may be applied to the second memory location than the first memory location. In some cases, data may be written to the second memory location during execution of a medical procedure routine from the first memory location. For example, some or all of the data generated by the medical procedure routine may be saved to the second memory location during execution of the routine. Similarly, data stored in the second memory location may be accessed by a user during execution of the medical procedure routine.

Process 400 may include storing installation data at the second memory location (block 406). In some implementations, the second memory location used to store operational data may also be used to store installation data. The installation data may include an installation program and/or other data files configured to add, remove, or update a medical procedure routine stored in the first memory location. Since access to the first memory location may be restricted, changes to the first memory location by the installation data may be restricted unless the medical device is in a service mode. Thus, the second memory location may be used as a staging ground to transfer data between the medical device and another device, without affecting a medical procedure routine stored in the first memory location. In other implementations, the installation program may be stored in another memory location, such as a third memory location.

Process 400 may include mirroring the first and second memory locations (block 408). The memory locations may be mirrored to any number of different memory partitions and/or storage devices. For example, the first storage location may be mirrored to a different storage device, to provide redundancy during execution of the medical procedure routine. Similarly, operational and/or installation data stored in the second memory location may be mirrored to another storage device, so that the exchange of data to and from the second memory location may remain uninterrupted in case of a storage device failure. Mirroring may be achieved via software and/or hardware, in various implementations. For example, a redundant array of disks (RAID) controller may be software-based or hardware-based, in various implementations.

Figure 5:
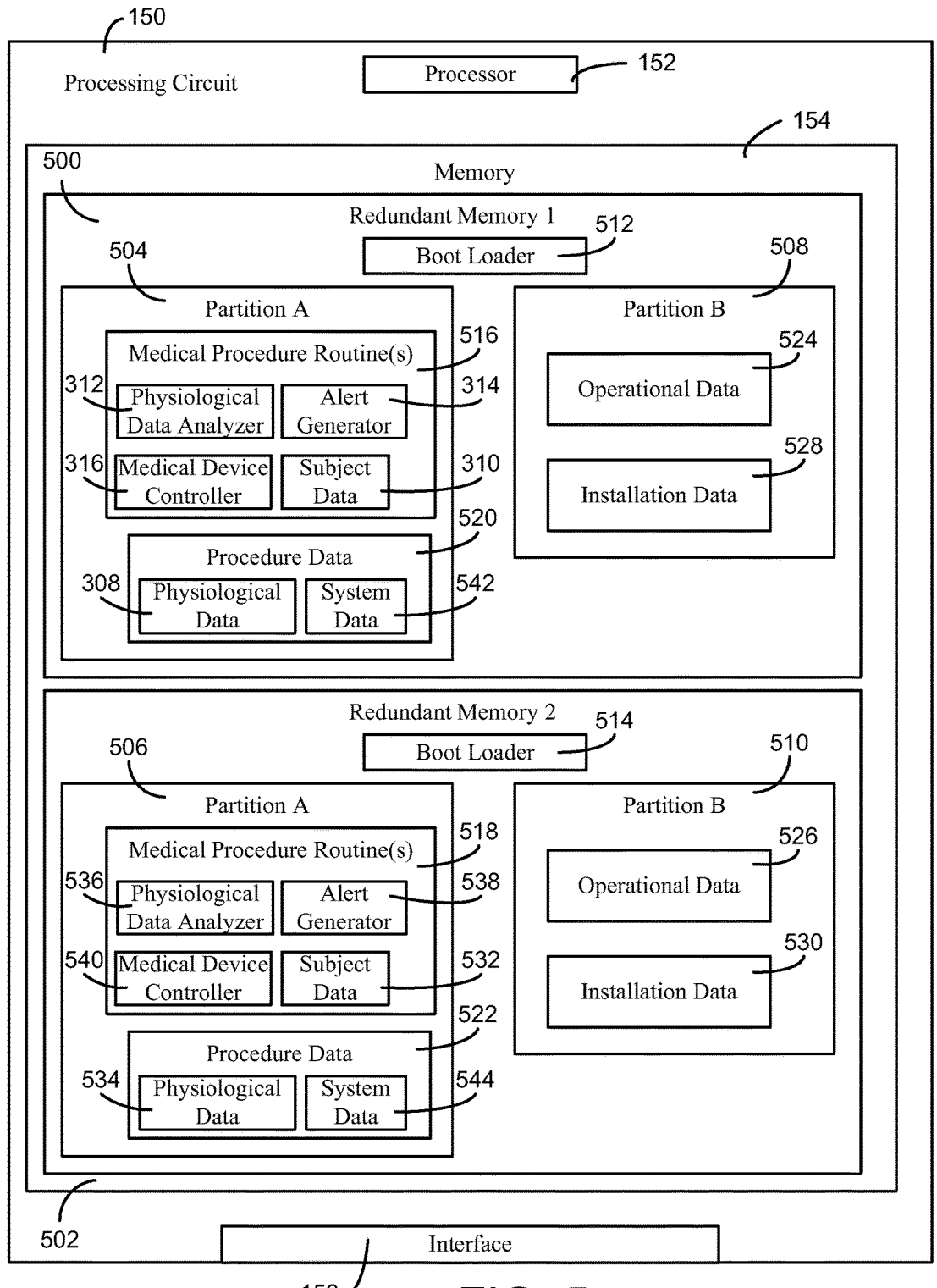
FIG. 5 is a block diagram of the processing circuit of FIG. 3 having redundant memory locations, in accordance with another exemplary implementation.

Referring now to FIG. 5, a block diagram of processing circuit 150 having redundant memory locations is shown, in accordance with another exemplary implementation. As shown in FIG. 5, data stored in memory 154 may be segregated based on whether the data is used in the performance of a medical procedure and/or is not critical to the performance of such a procedure. Any number of memory locations may be allocated for the segregated data stored in memory 154.

According to one implementation, a first partition 504 may store the one or more medical procedure routines 516 and procedure data 520, which may be any form of operational data generated or used during performance of the medical procedure. When executed by processor 152, a routine in routines 516 (e.g., medical device controller 516) may cause processing circuit 150 to generate and transmit control commands via interface 156 to one or more controlled devices. For example, processing circuit 150 may generate a control signal that causes a centrifuge to begin operation, if medical device 104 is an apheresis machine.

Medical procedure routines 516 may include physiological data analyzer 312, subject data 310, alert generator 314, medical device controller 316, or any other set of executable instructions or data that are processed by processor 154 during a medical procedure. In one implementation, subject data 310 may be used by medical procedure routines 516 during execution of a medical procedure on the subject. Likewise, procedure data 520 may include physiological data 308 generated during the procedure (e.g., physiological data regarding the subject of the procedure measured by a measurement device, such as measurement device 114). In a further implementation, procedure data 520 may include system data 542, which may include data regarding the state of the medical device generated during the procedure. For example, system data 542 may include event logs, errors, system metrics, or other forms of operational data generated during the execution of a procedure.

A second partition 508 may store any data that is not critical to the performance of the medical procedure. For example, partition 508 may include operational data 524 and/or installation data 528. Operational data 524 may include operational data collected during the most currently performed medical procedure (i.e., physiological data 308 or system data 542 may be transferred to partition 508 during or after the medical procedure completes, in various implementations). In some cases, operational data 524 may include operational data generated across a plurality of performed medical procedures. For example, operational data 524 may include any system events generated during startup of medical device 104 or operational data collected during two or more medical procedures. In one implementation, operational data 524 may include operational data from a measurement device, such as measurement device 114. Installation data 528 may be an executable program and/or any supporting data files configured to add, update, or remove a routine from medical procedure routines 516. For example, installation data 528 may include, but is not limited to, versions of physiological data analyzer 312, alert generator 314, medical device controller 316, or any other code executed during the procedure. In another example, installation data 528 may include subject data 310 regarding the particular subject of the procedure. For example, subject data 310 regarding the subject of the procedure may be downloaded to the medical device prior to the procedure and used by physiological data analyzer 312 during the procedure to adjust the operation of the device based on physiological data 308.

Memory 154 may also include a boot loader 512 configured to control the loading and execution of routines during startup of medical device 104. For example, boot loader 512 may load a routine at startup that causes processor 152 to perform a self-test of the components of medical device 104. In some implementations, boot loader 512 may be configured to launch the latest routine(s) stored in memory 154. For example, installation data 528 may be used to update a routine in routines 516. After medical device 104 is rebooted, boot loader 512 may cause the updated routine to be executed by processor 152.

In various implementations, different security settings may apply to partitions 504, 508. The settings may also depend on whether a medical procedure is currently being performed. For example, partition 504 may be password protected and may only be accessible when a medical procedure is not being performed by medical device 104. In some cases, the transfer of data between partition 504 and partition 508 may also be restricted. For example, procedure data 520 may be transferred from partition 504 to partition 508 during the performance of a medical procedure, but partition 508 may be prevented from writing data to partition 504 during this time. In some implementations, only certain data in procedure data 520 may be transferred to partition 508 during performance of a medical procedure. For example, smaller files in procedure data 520 may be transferred from partition 506 to operational data 524 in partition 508 during the medical procedure and larger files in procedure data 520 may be transferred at any other time (e.g., during startup, during shutdown, on completion of the medical procedure, in response to a request from a user, etc.). Larger files that may be transferred to operational data 524 outside of a medical procedure may include log files such as core files, activity audit trails, debugging files, etc. In other cases, smaller data files may also be transferred when a medical procedure is not being performed (e.g., in between the performance of medical procedures).

Installation data 528 may be prevented from modifying medical procedure routines 516 during the performance of a medical procedure. At other times, installation data 528 may be executed at startup, shutdown, during a service mode, or in response to receiving a request from a user of medical device 104. During a service mode, no restrictions may be placed on partition 508 transferring data to partition 504. For example, if an update is available via installation data 528, an alert may be provided to a display to notify an operator of medical device 104 that a software update is available. If the operator selects to update the software, medical device 104 may enter a service mode to begin the update (i.e., by modifying medical procedure routines 516). After installation, medical device 104 may remain in service mode to verify that the installation was successful. For example, medical device 104 may remain in service mode until a set of test sequences are completed, either manually or automatically (i.e., without further input from an operator). In some implementations, installation data 528 may install a software routine to partition 504 and partitions 504, 508 may swap functionality after installation (i.e., data needed to perform a medical procedure is now stored in partition 508 and non-critical data may now be stored in partition 504).

Processing circuit 150 may communicate with a remote device via interface 156 to perform any number of functions. In some implementations, operational data 524 may be transferred from medical device 104 to a remote device for storage and/or service of medical device 104. For example, a technician may analyze the received operational data to debug any potential problems during the operation of medical device 104. Since the data stored in memory 154 is segregated, operational data 524 may be transferred remotely even during the performance of a medical procedure, without significantly impacting the medical procedure.

In one example, procedure data 520 may be generated as an XML file when one of medical procedure routines 516 is executed, transferred to partition 508 from partition 504, and transferred to a remote device during execution of the routine. In a further example, the entirety of procedure data 520 may be transferred to operational data 524 after completion of the medical procedure and relayed to a remote device via interface 156. In some implementations, installation data 528 may be transferred to medical device 104 from the remote device via interface 156. For example, a technician may operate a device to make software and/or configuration changes to medical device 104 by installing, updating, or deleting certain software from medical device 104 via interface 156. In another example, the technician may update subject data 310 via a remote device (e.g., after the subject of the procedure checks in, information regarding the particular subject may be downloaded to the medical device for use during the procedure). In some implementations, some or all of the data transferred between processing circuit 150 and a remote device may be encrypted and sent over a secure connection.

The transfer of data between processing circuit 150 and a remote device via interface 156 may utilize a push or pull methodology. In some implementations, processing circuit 150 may transfer operational data 524 to a remote device in response to receiving a request for the data from the remote device. For example, a technician may operate the remote device to request log files and other forms of diagnostic data from processing circuit 150. Similarly, a user may operate medical device 104 to request software updates and other types of configuration data from a remote device. In other implementations, data may be transferred between processing circuit 150 and a remote device via a push methodology (i.e., without first receiving a request for the data from the other device). For example, operational data 524 may be transferred to a remote device in real-time, when operational data 524 is stored in partition 508. In some implementations, software qualification may be required to access memory 154 via a remote device. In other words, a software program running on the remote device requesting access to memory 154 may only be allowed access if it has valid credentials.

In various implementations, memory 154 may utilize any number of redundant storage devices. According to the implementation shown, memory 154 may include a first redundant memory 500 (e.g., a first data storage device) and a second redundant memory 502 (e.g., a second data storage device). For example, memories 500, 502 may be different hard drives in medical device 104. Data stored in memory 500 may be mirrored to memory 502. For example, memory 502 may include partitions 506, 510 and boot loader 514 that include the same data as partitions 504, 508, and boot loader 512, respectively. Thus, a copy of the one or more medical procedure routines 516 in partition 504 may be stored in partition 506 as medical procedure routines 518, and may include physiological data analyzer 536, alert generator 538, medical device controller 540, and subject data 532 mirrored from physiological data analyzer 312, alert generator 314, medical device controller 316, and subject data 310. Data generated by executing one of the medical procedure routines 516, i.e., procedure data 520, may also be mirrored to memory 502 as procedure data 522, including physiological data 534 and system data 544 mirrored from physiological data 508 and system data 542. If a device failure occurs in memory 500, processor 152 may switch to the mirrored data stored in memory 502, so that operation of the medical device 104 is not impeded. Similarly, operational data 524 and installation data 528 in partition 508 may be mirrored to partition 510 of memory 502. In some implementations, memory 500 and memory 502 may swap functionality (i.e., memory 502 may be converted from the mirrored memory to being the primary storage device). For example, installation data 530 may be transferred to memory 502 instead of memory 500 while memory 500 is acting as the primary memory. Installation data 530 may then be executed to update medical procedure routines 518 in memory 502 and memory 502 may become the primary memory (i.e., data stored in memory 502 may then be mirrored to memory 500).

In other implementations, partitions 504-510 and/or the data within them may be stored in separate storage devices. Thus, a failure in the device of partition 504 may not affect the functioning of the device of partition 508. However, the financial cost of memory 154 may increase as additional memory devices are used in processing circuit 150. In some implementations, three partitions may be used to store data in memory 154, e.g., a first partition for application data, a second partition for communication data, and a third partition to store operational data such as log files, configuration data, procedure data, etc. In case of a failure from the first partition to the second partition, the data files stored in the third partition would not need to be replicated.

Figure 6:
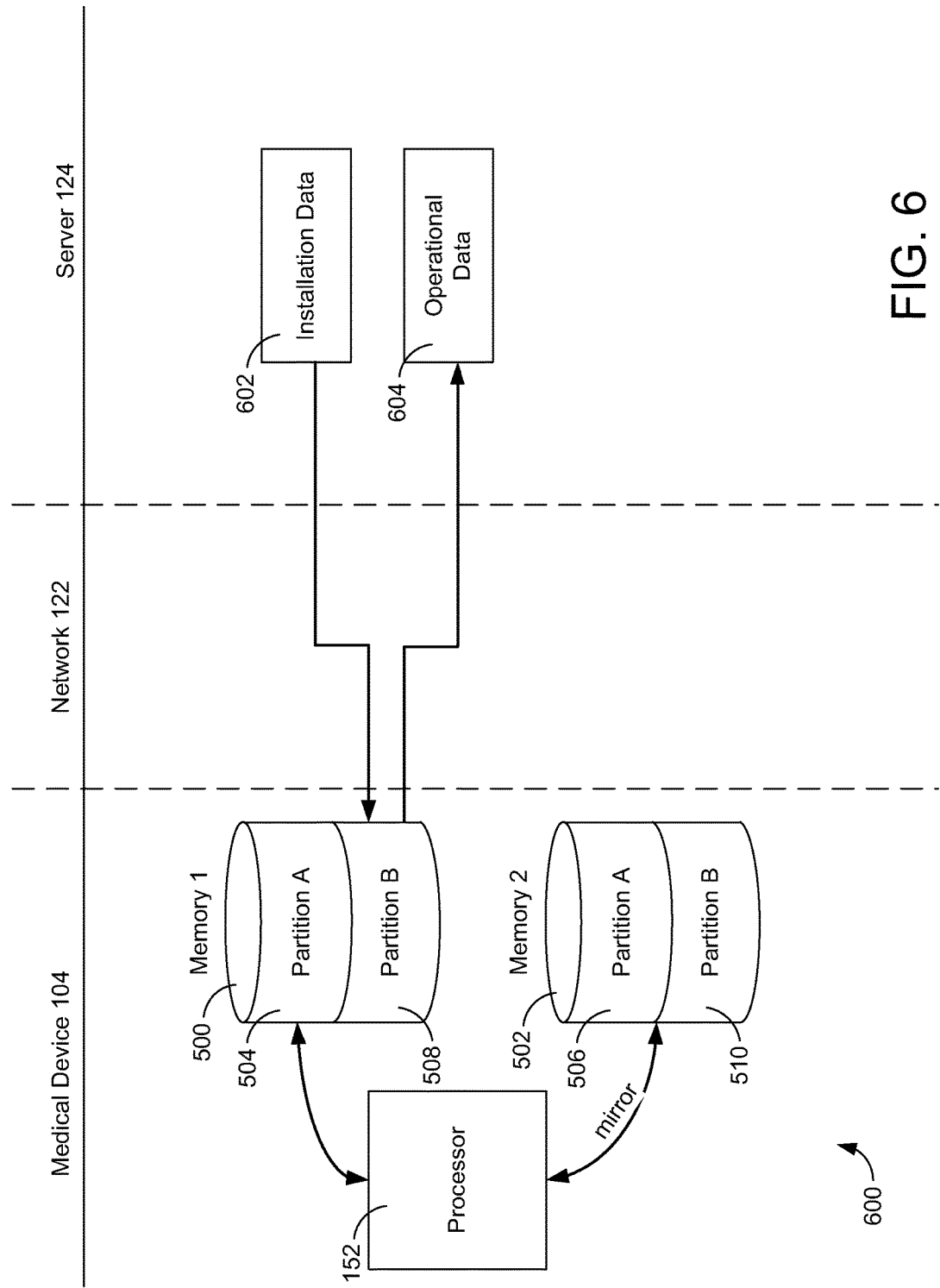
FIGS. 6-8 are illustrations of a medical device communicating with a server, in accordance with various exemplary implementations.
Figure 7:
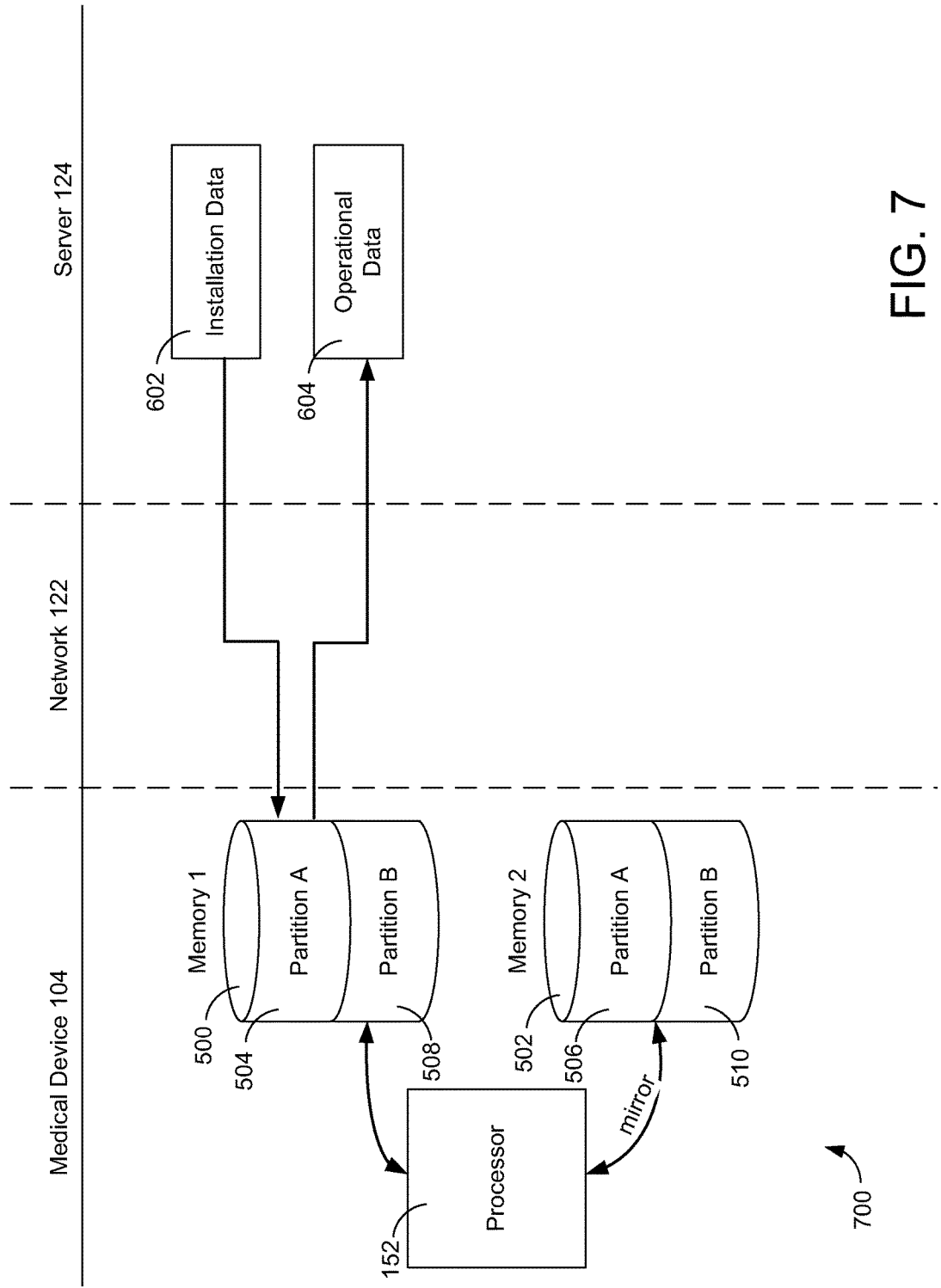
Figure 8:
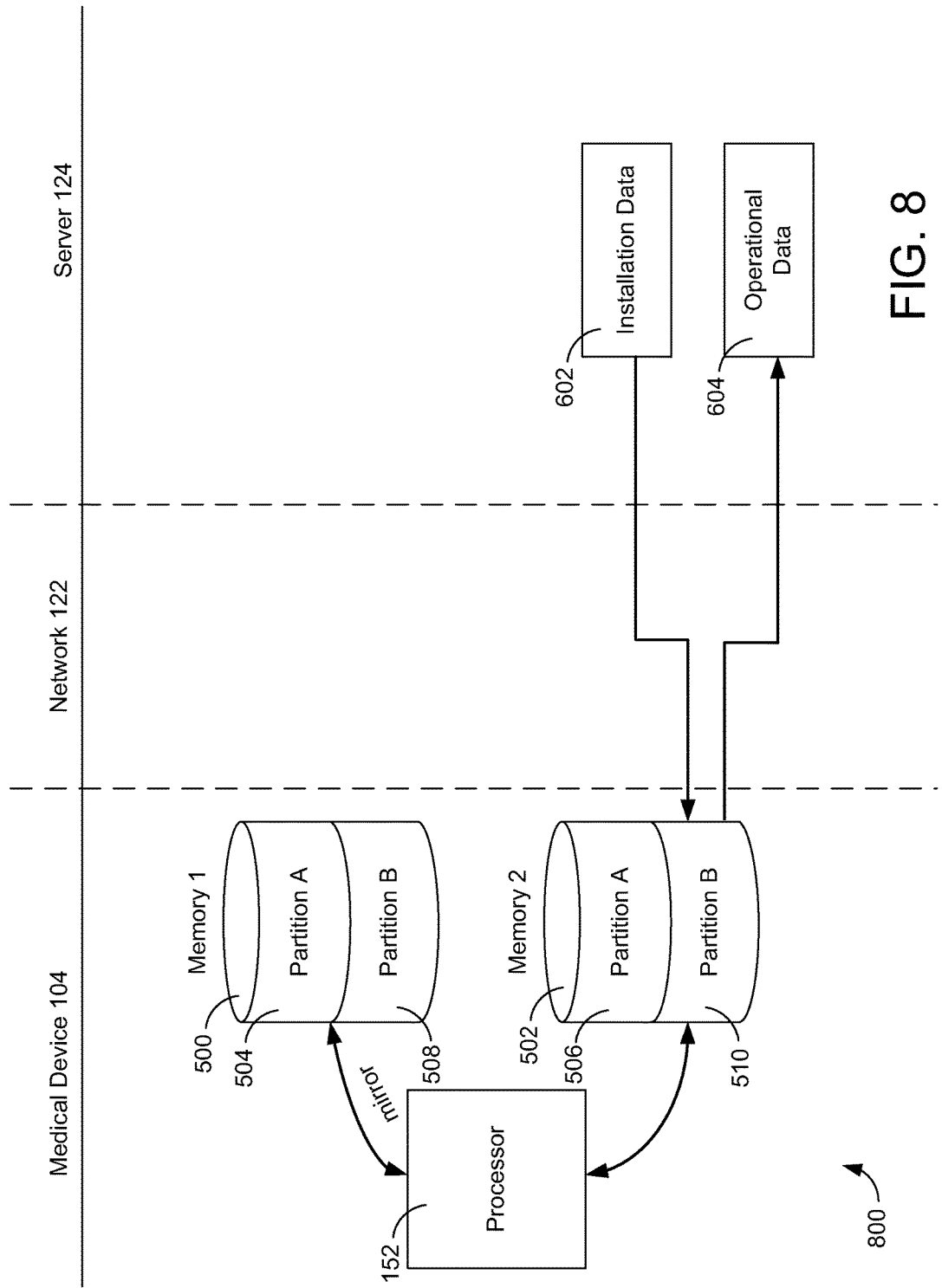

Referring now generally to FIGS. 6-8, illustrations are shown of various implementations that utilize data segregation and redundancy within medical device 104. In the illustrations shown, data may be transmitted between medical device 104 and a remote device, such as server 124, via network 122. For example, operational data may be generated by medical device 104 and transferred to server 124. As shown in the various illustrations, processor 152 of medical device 104 may be in communication with separate memory devices 500, 502, which make up the total memory 154 of the device. Memory 500 may be partitioned into partitions 504, 508 and memory 502 may be partitioned into partitions 506, 510. Operational data 604, such as log files, debug data, measured physiological data, and other data generated while medical device 104 is operating may be transferred from medical device 104 to server 124 via network 122. Similarly, server 124 may transfer installation data 602 to medical device 104 via network 122, to reconfigure the software installation on medical device 104.

In FIG. 6, illustration 600 depicts an implementation in which memory 500 is a primary memory and any changes to the data stored in memory 500 are mirrored to memory 502. For example, data written to memory 500 may also be written to memory 502, to provide redundancy. In the implementation shown, each of memories 500, 502 may be partitioned into separate partitions for data used during administration of a medical procedure and for data that is not critical to performing the procedure. As shown, partitions 504, 506 may store the data needed to perform the medical procedure and partitions 508, 510 may store the non-critical data. Since memory 500 is the primary memory, processor 152 may execute a medical procedure routine from partition 504 and may use partition 508 to store data communicated between medical device 104 and server 124. For example, operational data 604 may be transmitted from partition 508 to server 124 and installation data 602 may be transmitted from server 124 to partition 508.

In FIG. 7, illustration 700 depicts another implementation in which memory 500 is a primary memory and any changes to the data stored in memory 500 are mirrored to memory 502. For example, data written to memory 500 may also be written to memory 502, to provide redundancy. Similar to the implementation of FIG. 6, memories 500, 502 may be partitioned into separate partitions for data used during administration of a medical procedure and for data that is not critical to performing the procedure. As shown in FIG. 7, however, partitions 508, 510 may store the data needed to perform the medical procedure and partitions 504, 506 may store the non-critical data. Since memory 500 is still the primary memory, processor 152 may execute a medical procedure routine from partition 508 and may use partition 506 to store data communicated between medical device 104 and server 124. Therefore, operational data 604 may be transmitted from partition 504 to server 124 and installation data 602 may be transmitted from server 124 to partition 504.

In FIG. 8, illustration 800 depicts another implementation in which memory 502 is the primary memory and any changes to the data stored in memory 502 are mirrored to memory 500 for purposes of redundancy. Similar to the implementations of FIGS. 6-7, memories 500, 502 may be partitioned into separate partitions 504, 506 that store the data used during administration of a medical procedure and partitions 508, 510 that store the non-critical data. Since memory 502 is the primary memory in the implementation shown, processor 152 may execute a medical procedure routine from partition 506 and use partition 510 to store data communicated between medical device 104 and server 124. In other words, operational data 604 may be transmitted from partition 510 to server 124 and installation data 602 may be transmitted from server 124 to partition 510.

According to various implementations, medical device 104 may alternate between the implementations depicted in FIGS. 6-8. In one example, assume that memory 500 is the primary memory, as shown in illustrations 600, 700. If a failure occurs in memory 500, medical device 104 may switch to using memory 502 as the primary memory, as shown in illustration 800. In such a case, execution of a medical procedure routine may continue in an uninterrupted fashion by continuing execution of the routine from memory 502.

In further examples, medical device 104 may alternate between the implementations depicted in FIGS. 6-8 after making a software change (e.g., installing a software update, removing software, etc.). For example, assume that installation data 602 is used in the implementation shown in illustration 600 to install an updated version of a medical procedure routine to partition 508, instead of partition 504. After a successful installation of the routine to partition 508, medical device 104 may begin using partition 508 to perform the corresponding medical procedure and partition 504 to store non-critical data, as shown in illustration 400. Alternatively, installation data 602 shown in illustration 600 may be operable to install the medical procedure routine to memory 502. After successful installation, medical device 104 may begin using memory 502 as the primary memory and mirror data changes to memory 502 to memory 500, as shown in illustration 800.

Figure 9:
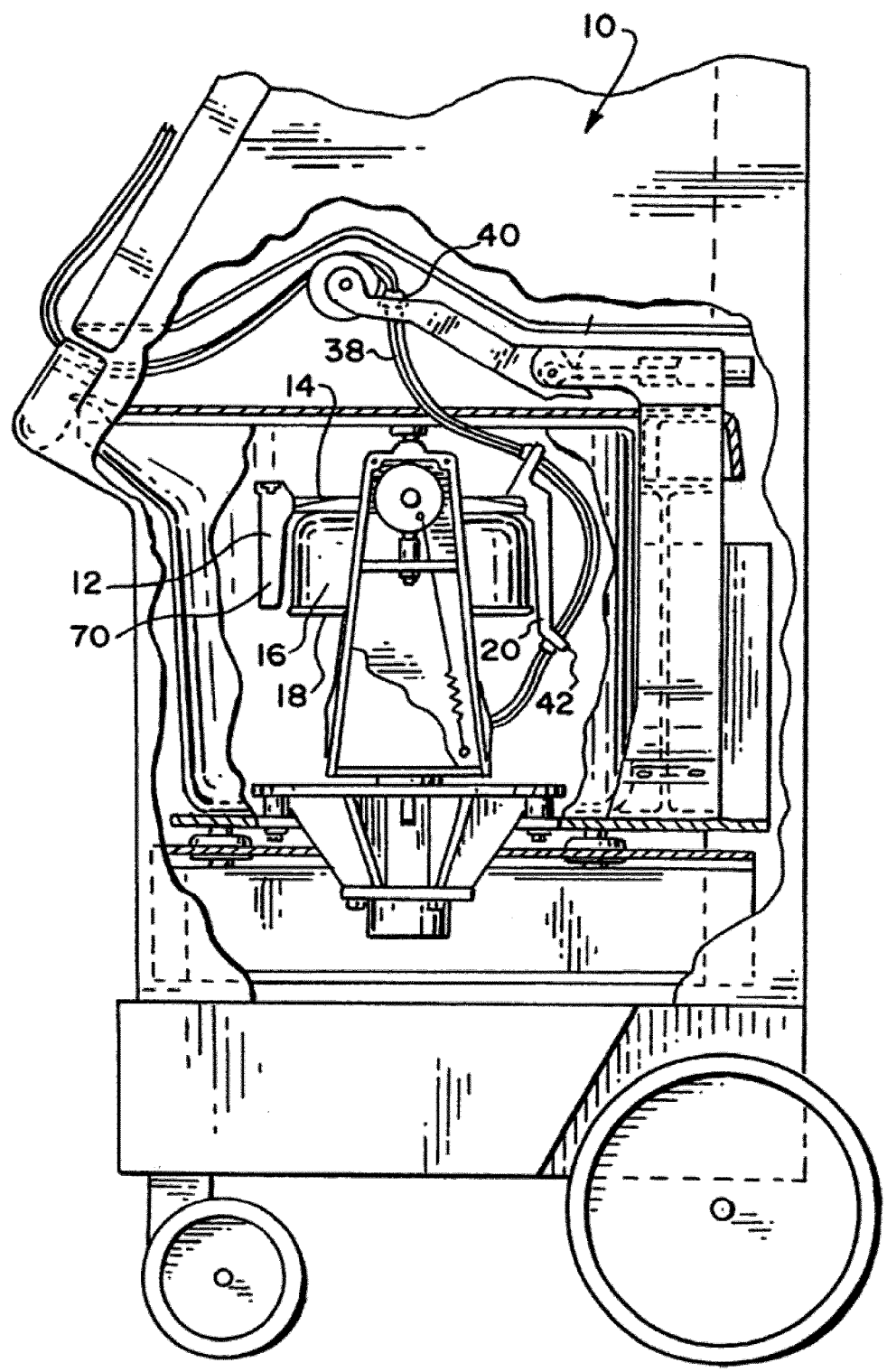
FIGS. 9-10 are side elevation views, with portions broken away and in section, of an apheresis machine, according to an exemplary implementation.
Figure 10:
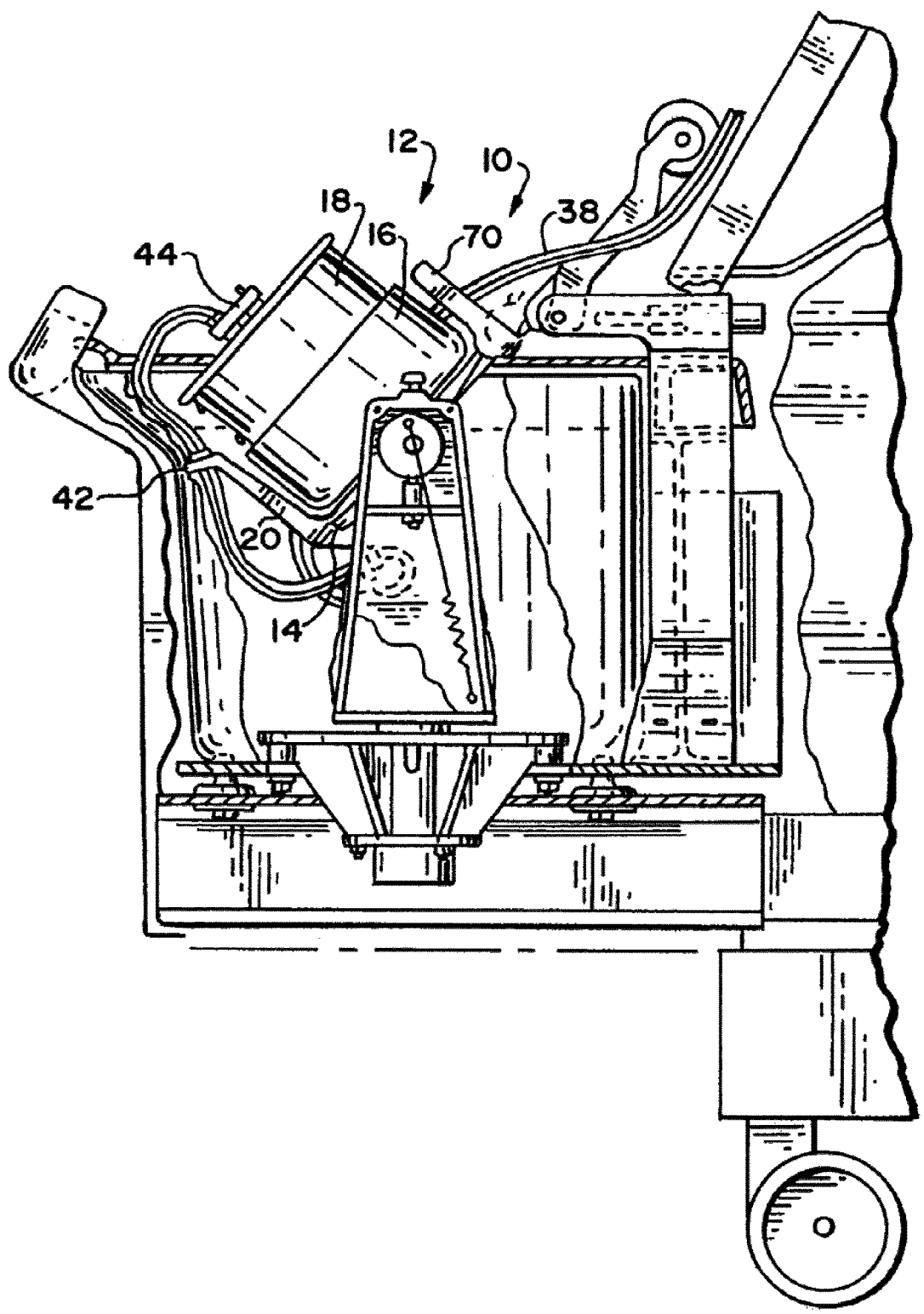

Referring now to FIGS. 9-10, an apheresis machine 10 is shown, according to an exemplary embodiment. Apheresis machine 10 includes a separation component 14 used to separate blood components. Separation component 14 may be, for example, a centrifuge or spinning membrane configured to separate blood components. According to various embodiments, separation component 14 may be controlled by a processing circuit, such as processing circuit 150 shown in FIG. 3 or FIG. 5, via an interface controller 12. In the illustrated embodiment, the separation component 14 separates whole blood to harvest red blood cells (RBC), platelet concentrate (PC), and platelet-poor plasma (PPP). Separation component 14 can also be used to harvest mononuclear cells and granulocytes from blood. Separation component 14 may include a spool holder 16 and a spool 18. Spool holder 16 and spool 18 are pivoted on a yoke 20 between an upright position, as FIG. 10 shows, and a suspended position, as FIG. 9 shows. When upright, spool 18 can be opened by movement at least partially out of the spool holder 16, as FIG. 10 shows. In this position, the operator wraps a flexible blood processing chamber (not shown) about the spool 18. Closure of the spool 18 and spool holder 16 encloses the chamber for processing. When closed, the spool 18 and spool holder 16 are pivoted into the suspended position for rotation about an axis. Apheresis machine 10 further includes a tubing umbilicus connecting components located outside the rotating components of separation component 14. A non-rotating holder 40 holds the upper portion of umbilicus 38 in a non-rotating position above spool 18 and spool holder 16. A holder 42 on yoke 20 rotates the midportion of umbilicus 38 at a first speed about spool 18 and spool holder 16, and another holder 44 rotates the lower end of umbilicus 38 at a second speed twice the first speed at which spool 18 and spool holder 16 rotate. Interface controller 12 may include a viewing head carried on yoke 20.

Implementations of the subject matter and the operations described in this specification can be implemented in digital electronic circuitry, or in computer software, firmware, or hardware, including the structures disclosed in this specification and their structural equivalents, or in combinations of one or more of them. Implementations of the subject matter described in this specification can be implemented as one or more computer programs, i.e., one or more modules of computer program instructions, encoded on one or more computer storage medium for execution by, or to control the operation of, data processing apparatus. Alternatively or in addition, the program instructions can be encoded on an artificially-generated propagated signal, e.g., a machine-generated electrical, optical, or electromagnetic signal, that is generated to encode information for transmission to suitable receiver apparatus for execution by a data processing apparatus. A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially-generated propagated signal. The computer storage medium can also be, or be included in, one or more separate components or media (e.g., multiple CDs, disks, or other storage devices). Accordingly, the computer storage medium may be tangible.

The operations described in this specification can be implemented as operations performed by a data processing apparatus on data stored on one or more computer-readable storage devices or received from other sources.

The term "client or "server" include all kinds of apparatus, devices, and machines for processing data, including by way of example a programmable processor, a computer, a system on a chip, or multiple ones, or combinations of the foregoing. The apparatus can include special purpose logic circuitry, e.g., an FPGA (field programmable gate array) or an ASIC (application-specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub-programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform actions by operating on input data and generating output. The processes and logic flows can also be performed by, and apparatus can also be implemented as, special purpose logic circuitry, e.g., an FPGA (field programmable gate array) or an ASIC (application specific integrated circuit).

While this specification contains many specific implementation details, these should not be construed as limitations on the scope of any inventions or of what may be claimed, but rather as descriptions of features specific to particular implementations of particular inventions. Certain features that are described in this specification in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems can generally be integrated together in a single software product or packaged into multiple software products.

Thus, particular implementations of the subject matter have been described. Other implementations are within the scope of the following claims. In some cases, the actions recited in the claims can be performed in a different order and still achieve desirable results. In addition, the processes depicted in the accompanying figures do not necessarily require the particular order shown, or sequential order, to achieve desirable results. In certain implementations, multitasking or parallel processing may be utilized.

What is claimed is:

1. A method for using physiological data to control an apheresis machine, the apheresis machine comprising a processing circuit including a processor and a memory, the processor configured to execute instructions stored in the memory, the memory including a first memory partition including a control module for generating commands for controlling the apheresis machine and a first procedure data module storing a medical procedure routine, and a second memory partition including a second procedure data module, the method comprising:
   generating a start procedure command at the control module based on the medical procedure routine;
   causing the apheresis machine to begin a medical procedure on a subject based on the start procedure command generated at the control module, wherein the medical procedure is an apheresis procedure;
   in response to causing the medical device to begin the medical procedure and receiving a data change request, determining whether the medical procedure routine is executing and whether the data change request is received from the medical procedure routine;
   in response to determining that the medical procedure routine is executing and the data change request is received from the medical procedure routine, changing data stored in the first memory partition while the medical procedure routine is executing;
   storing, in the second procedure data module, physiological data received from a measurement device, the physiological data being indicative of a physiological condition of the subject during the medical procedure, the physiological data including at least one of a measured blood pressure, body temperature, respiratory rate, or pulse rate of the subject;
   analyzing, by the control module, the physiological data;
   generating, by the control module, a control command for the apheresis machine based in part on the analyzed physiological data, wherein the control command causes the apheresis machine to adjust a flow rate of blood through the apheresis machine;
   modifying operation of the medical procedure by the apheresis machine based on the control command by adjusting the flow rate of blood through the apheresis machine.

2. A system for using physiological data comprising:
   an apheresis machine configured to perform a medical procedure on a subject, wherein the medical procedure comprises administering a medicament to the subject at an infusion rate, pausing the medical procedure, or aborting the medical procedure; and
   a medical device controller including:
      a processor and a memory, the processor configured to execute instructions stored in the memory, the memory including a first memory partition and a second memory partition;
      the first memory partition including a control module configured to generate a start procedure command configured to cause the apheresis machine to begin the medical procedure on a subject, and a first procedure data module; and
      the second memory partition including a second procedure data module configured to receive physiological data from a measurement device, the physiological data being indicative of a physiological condition of the subject during the medical procedure, and store the physiological data in the second procedure data module;
   wherein the control module is further configured to:
      analyze the physiological data stored in the second procedure data module;
      generate a control command for the apheresis machine based in part on the analyzed physiological data, wherein the control command causes the apheresis machine to adjust the infusion rate of the medicament to the subject in response to receiving the control command;
      cause the apheresis machine to modify operation of the medical procedure based on the control command; and
      determine whether the apheresis machine is performing the medical procedure, in response to determining that the medical device is performing the medical procedure, apply a first read/write permission to prevent data from being written to the first memory partition, and in response to determining that the medical device is not performing the medical procedure, apply a second read/write permission to allow data to be written to the first memory partition.

3. The method of claim 1, further comprising:
   storing, in an installation data module of the second memory partition, installation data configured to alter the control module;
   in response to causing the medical device to begin the medical procedure, preventing the installation data from accessing the first memory partition during the medical procedure; and
   in response to causing the medical device to end the medical procedure and causing the medical device to enter a service mode, allowing the installation data to alter the control module.

4. The method of claim 3, further comprising:
   mirroring the first memory partition to a redundant memory by storing a copy of the control module in the redundant memory, wherein the first memory partition is stored on a first data storage device and the redundant memory comprises a second data storage device; and
   mirroring the second memory partition to the redundant memory, wherein the second memory partition is stored on the first data storage device.

5. The method of claim 4, further comprising:
   using the installation data to alter the control module and the mirrored control module;
   designating the mirrored first memory partition as a primary partition; and
   using the mirrored control module in the primary partition to perform a second medical procedure.

6. The system of claim 2, wherein the medical procedure comprises an apheresis procedure and the medicament comprises at least one of: an anticoagulant, blood replacement fluid, or bolus of saline.

7. The system of claim 2, wherein the physiological data comprises at least one of a measured blood pressure, body temperature, respiratory rate, or pulse rate of the subject.

8. The system of claim 7, wherein the control command causes the an apheresis machine to administer a medicament comprising at least one of a bolus of saline, an anticoagulant, or a blood replacement fluid.

9. The system of claim 2, wherein the control module is further configured to:

store, in an installation data module of the second memory partition, installation data configured to alter the control module;

in response to causing the apheresis machine to begin the medical procedure, prevent the installation data from accessing the first memory partition during the medical procedure; and in response to causing the apheresis machine to end the medical procedure and causing the apheresis machine to enter a service mode, allow the installation data to alter the control module when the apheresis machine is in the service mode.

10. The system of claim 9, wherein the control module is further configured to:

mirror the first memory partition to a redundant memory by storing a copy of the control module in the redundant memory, wherein the first memory partition is stored on a first data storage device and the redundant memory comprises a second data storage device; and mirror the second memory partition to the redundant memory, wherein the second memory partition is stored on the first data storage device.

11. The method of claim 1, wherein: the physiological data includes at least two data measurements indicative of the physiological condition of the subject; analyzing the physiological data further includes parsing the physiological data to select only one data measurement; and the control command is configured to reduce a difference between a subsequent data measurement and the setpoint.

12. The system of claim 2, wherein: the physiological data includes at least two data measurements indicative of the physiological condition of the subject; the control module is further configured to parse the physiological data to select only one data measurement; and the control command is configured to reduce a difference between a subsequent data measurement and the setpoint.

13. A system for using physiological data comprising:

an apheresis machine configured to perform an apheresis procedure on a subject; and a medical device controller including:

a processor and a memory, the processor configured to execute instructions stored in the memory, the memory including a first memory partition and a second memory partition;

the first memory partition including a control module configured to generate a start procedure command configured to cause the apheresis machine to begin the apheresis procedure on the subject, and a first procedure data module storing a medical procedure routine; and the second memory partition including a second procedure data module configured to receive physiological data from a measurement device, the physiological data being indicative of a physiological condition of the subject during the apheresis procedure, and store the physiological data in the second procedure data module;

wherein the control module is further configured to:

analyze the physiological data stored in the second procedure data module;

generate a control command for the apheresis machine based in part on the analyzed physiological data;

cause the apheresis machine to modify operation of the apheresis procedure based on the control command; and require a security credential to access the first memory partition during execution of the medical procedure routine.

* * * * *